US012575809B2

(12) United States Patent
McLeod

(10) Patent No.: US 12,575,809 B2
(45) Date of Patent: Mar. 17, 2026

(54) METHOD AND SYSTEM FOR DEFINING A BOUNDARY OF A REGION OF INTEREST BY APPLYING THRESHOLD VALUES TO OUTPUTS OF A PROBABILISTIC AUTOMATIC SEGMENTATION MODEL BASED ON USER-SELECTED SEGMENTATION SENSITIVITY LEVELS

(71) Applicant: GE Precision Healthcare LLC, Wauwatosa, WI (US)

(72) Inventor: Kristin Sarah McLeod, Oslo (NO)

(73) Assignee: GE Precision Healthcare LLC, Waukesha, WI (US)

( * ) Notice: Subject to any disclaimer, the term of this patent is extended or adjusted under 35 U.S.C. 154(b) by 595 days.

(21) Appl. No.: 17/880,490

(22) Filed: Aug. 3, 2022

(65) Prior Publication Data

US 2024/0041430 A1     Feb. 8, 2024

(51) Int. Cl.
    *G06T 7/11*        (2017.01)
    *A61B 8/00*        (2006.01)
    *G06T 7/136*       (2017.01)

(52) U.S. Cl.
    CPC .............. *A61B 8/469* (2013.01); *A61B 8/465* (2013.01); *G06T 7/11* (2017.01)

(58) Field of Classification Search
    None
    See application file for complete search history.

(56) References Cited

U.S. PATENT DOCUMENTS

| | | | | |
|---|---|---|---|---|
| 2009/0132916 A1* | 5/2009 | Filatov | ................... | G16H 40/63 |
| | | | | 715/700 |
| 2012/0320055 A1* | 12/2012 | Pekar | ...................... | G06T 7/143 |
| | | | | 345/424 |
| 2013/0287283 A1* | 10/2013 | Kamath | ................... | G06F 18/40 |
| | | | | 345/589 |
| 2020/0320774 A1* | 10/2020 | Imasugi | ................ | G06T 15/205 |
| 2021/0241016 A1* | 8/2021 | Hashimoto | ............. | G01T 1/161 |
| 2022/0415013 A1* | 12/2022 | Yoo | ...................... | G06V 10/761 |

FOREIGN PATENT DOCUMENTS

KR         20210110183        *  9/2021   ............... A61B 6/12

* cited by examiner

*Primary Examiner* — Beniyam Menberu
(74) *Attorney, Agent, or Firm* — McAndrews, Held & Malloy, Ltd.; Daniel Bissing; David Bates

(57) ABSTRACT

Systems and methods for defining a boundary of a region of interest in an ultrasound image are provided. The method includes receiving an ultrasound image having pixels and automatically processing the ultrasound image to output a probability of each of the pixels being in a region of interest. The method includes applying a first threshold value to determine a boundary of the region of interest. The first threshold value corresponds with a first segmentation sensitivity level of a plurality of segmentation sensitivity levels. The method includes displaying the ultrasound image with the boundary overlaid on the ultrasound image. The method includes receiving a user selection of a second segmentation sensitivity level that corresponds with a second threshold value different from the first threshold value, and dynamically updating the boundary overlaid on the ultrasound image at the display based on the second threshold value.

19 Claims, 4 Drawing Sheets

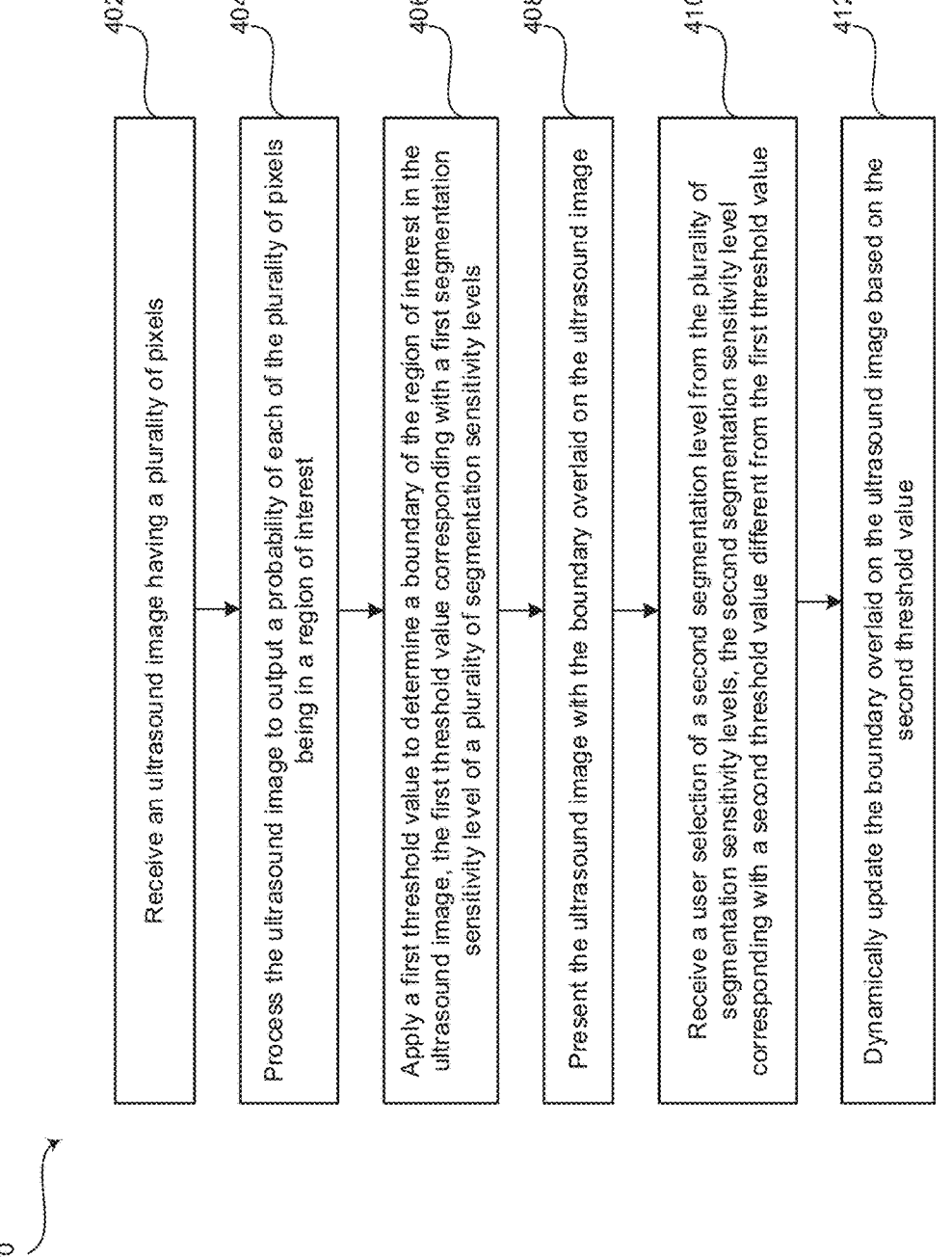

402 Receive an ultrasound image having a plurality of pixels

404 Process the ultrasound image to output a probability of each of the plurality of pixels being in a region of interest 406 Apply a first threshold value to determine a boundary of the region of interest in the ultrasound image, the first threshold value corresponding with a first segmentation sensitivity level of a plurality of segmentation sensitivity levels 408 Present the ultrasound image with the boundary overlaid on the ultrasound image 410 Receive a user selection of a second segmentation level from the plurality of segmentation sensitivity levels, the second segmentation sensitivity level corresponding with a second threshold value different from the first threshold value 412 Dynamically update the boundary overlaid on the ultrasound image based on the second threshold value

METHOD AND SYSTEM FOR DEFINING A BOUNDARY OF A REGION OF INTEREST BY APPLYING THRESHOLD VALUES TO OUTPUTS OF A PROBABILISTIC AUTOMATIC SEGMENTATION MODEL BASED ON USER-SELECTED SEGMENTATION SENSITIVITY LEVELS

FIELD

Certain embodiments relate to ultrasound imaging. More specifically, certain embodiments relate to a method and system for defining a boundary of a region of interest in an ultrasound image by applying a threshold value corresponding to a user-selected segmentation sensitivity level to outputs of a probabilistic automatic segmentation model.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Ultrasound imaging may involve the segmentation of regions of interest in ultrasound images for analysis and diagnosis. Image analysis techniques, such as computer vision, artificial intelligence, and the like, may be applied to segment regions of interest by processing an ultrasound image to determine a probability that each pixel of the image is within a region of interest, and applying a single, fixed threshold to define the boundary of the region of interest. Accordingly, these image analysis techniques are typically static in nature. The static nature of the image analysis techniques provides a lack of dynamic adaptability of the processing for different users, types of regions of interest, and/or types of ultrasound examinations, thereby limiting the use of the image analysis technique to a particular user and/or application. For example, different users may prefer different delineations (e.g., thicker or thinner) of regions of interest in an ultrasound image. As another example, users may prefer different delineations depending on the region of interest being segmented and/or the type of ultrasound examination.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for defining a boundary of a region of interest in an ultrasound image by applying a threshold value corresponding to a user-selected segmentation sensitivity level to outputs of a probabilistic automatic segmentation model, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 4 is a flow chart illustrating exemplary steps that may be utilized for defining a boundary of a region of interest in an ultrasound image by applying a threshold value corresponding to a user-selected segmentation sensitivity level to outputs of a probabilistic automatic segmentation model, in accordance with various embodiments.

DETAILED DESCRIPTION

Figure 1:
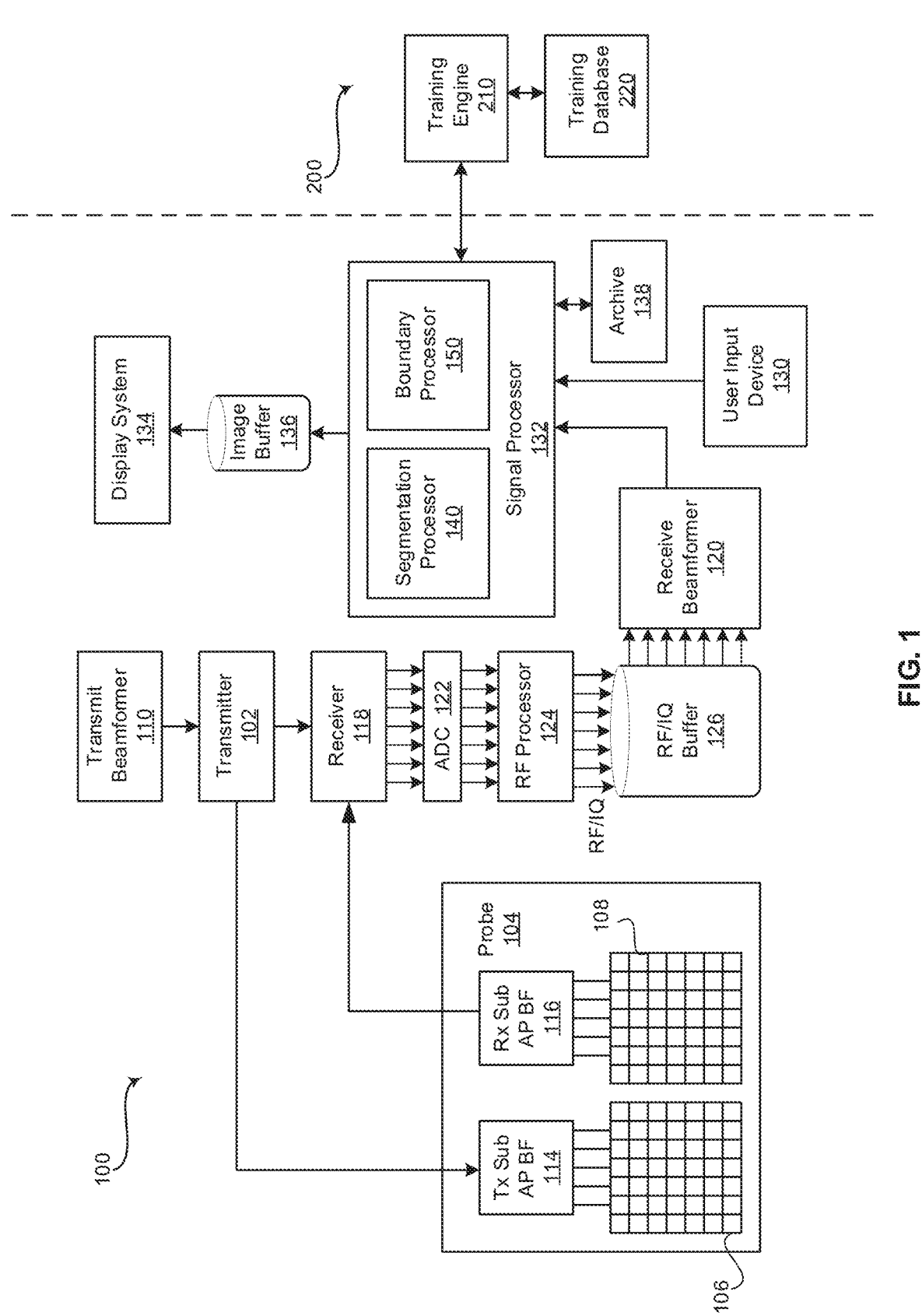
FIG. 1 is a block diagram of an exemplary ultrasound system that is operable to define a boundary of a region of interest in an ultrasound image by applying a threshold value corresponding to a user-selected segmentation sensitivity level to outputs of a probabilistic automatic segmentation model, in accordance with various embodiments.

Certain embodiments may be found in a method and system for defining a boundary of a region of interest in an ultrasound image by applying a threshold value corresponding to a user-selected segmentation sensitivity level to outputs of a probabilistic automatic segmentation model. Aspects of the present disclosure have the technical effect of providing a plurality of user-selectable segmentation sensitivity levels applied to define a boundary of region of interest. Various embodiments provide the technical effect of dynamically updating a boundary of a region of interest in response to a user-selection of one of a plurality of segmentation sensitivity levels. Certain embodiments provide the technical effect of providing a plurality of presets, each of the plurality of presets associated with a different segmentation sensitivity level having a corresponding threshold value applied to outputs of a probabilistic automatic segmentation model to define a boundary of a region of interest. Aspects of the present disclosure have the technical effect of updating a default threshold value to correspond with a last selected segmentation sensitivity level. Various embodiment provide the technical effect of storing a threshold value corresponding with a last selected segmentation sensitivity level in association with a particular user and/or a particular ultrasound system. Certain embodiments provide the technical effect of providing user interface tools presented at a display system with an ultrasound image overlaid with a boundary of a region of interest, the user interface tools configured to receive a user input for selecting a different segmentation sensitivity level having a threshold value applied to outputs of a probabilistic automatic segmentation model to dynamically update the boundary overlaid on the ultrasound image.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CELTS), and/or sub-modes of B-mode and/or CF such as Harmonic Imaging, Shear Wave Elasticity Imaging (SWEI), Strain Hastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to define a boundary of a region of interest in an ultrasound image by applying a threshold value corresponding to a user-selected segmentation sensitivity level to outputs of a probabilistic automatic segmentation model, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two-dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a heart, a fetus, a uterus, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or a plurality of AD converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RE processor 124 may comprise suitable logic, circuitry, interfaces and/or code that may be operable to demodulate the digital signals output by the plurality of A/D converters 122. In accordance with an embodiment, the RE processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RE or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RE processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, image acquisition and scan parameters, settings, configuration parameters, select protocols and/or templates, change scan mode, select one of a plurality of segmentation sensitivity levels, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RE processor 124, the RE/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a segmentation processor 140 and a boundary processor 150, and may be capable of receiving input information from a user input device 130 and/or archive 138, generating an output displayable by a display system 134, and manipulating the output in response to input information from a user input device 130, among other things. The signal processor 132, segmentation processor 140, and boundary processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately, Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a segmentation processor 140 that comprises suitable logic, circuitry, interfaces and/or code that may be operable to receive an ultrasound image having a plurality of pixels. The segmentation processor 140 may be configured to automatically process the ultrasound image to output a probability of each of the plurality of pixels in the ultrasound image being in the region of interest. For example, the segmentation processor 140 may comprise a probabilistic automatic segmentation model that receives the ultrasound image having the plurality of pixels and outputs the probability of each pixel being part of the region of interest. The region of interest may be an anatomical structure, an artificial structure, measurement endpoints, or the like. For example, the region of interest may be an anatomical structure, such as a heart chamber (e.g., left ventricle), endometrium, fetal head, blood vessel, or any suitable anatomical structure. As another example, the region of interest may be an artificial structure such as a needle, or any suitable artificial structure. As another example, the region of interest may be measurement endpoints, such as ends of a femur of a fetus to provide a femur length measurement or any suitable measurement endpoints.

The segmentation processor 140 may include a probabilistic automatic segmentation model comprising image analysis algorithms, artificial intelligence algorithms, computer vision algorithms, one or more deep neural networks (e.g., a convolutional neural network) and/or may utilize any suitable form of image analysis techniques or machine learning processing functionality configured to automatically process and output probabilities that pixels of an ultrasound image are part of a region of interest. The probabilistic automatic segmentation model executed by the segmentation processor 140 may provide the outputted probabilities to the boundary processor 150 for generating a boundary of the region of interest superimposed on the ultrasound image and presented at the display system 134 and/or store the probabilities at archive 138 and/or any suitable data storage medium.

In various embodiments, the probabilistic automatic segmentation model executed by the segmentation processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the probabilistic automatic segmentation model executed by the segmentation processor 140 may include an input layer having a neuron for each pixel or a group of pixels from an ultrasound image, such as an echocardiogram ultrasound scan. The output layer may have neurons corresponding to probabilities that each of the pixels is part of a region of interest, such as a left ventricle of a heart. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the segmentation processor 140 deep neural network (e.g., convolutional neural network) may output region of interest pixel probabilities in an ultrasound image with a high degree of accuracy.

The signal processor 132 may include a boundary processor 150 that comprises suitable logic, circuitry, interfaces and/or code that may be operable to receive from the segmentation processor 140, or retrieve from archive 138 and/or any suitable data storage medium, the probabilities that each pixel in the ultrasound image is part of the region of interest. The boundary processor 150 may be configured to apply a threshold corresponding to one of a plurality of segmentation sensitivity levels to determine a boundary of the region of interest. Each of the plurality of segmentation sensitivity levels correspond with a different threshold. For example, the plurality of segmentation sensitivity levels may comprise two (2), three (3), five (5), ten (10), or any suitable number of segmentation sensitivity levels. The plurality of segmentation sensitivity levels may be distinguished by number (e.g., 1, 2, 3, etc.), letter (e.g., A, B, C, etc.), name (e.g., low, medium, high, etc.), a position on a user interface tool presented at the display system (e.g., top of a scroll bar, middle of a scroll bar, bottom of a scroll bar, etc.), or any suitable distinguishing feature.

The thresholds associated with each of the segmentation sensitivity levels are applied by the boundary processor 150 to determine the pixels of the ultrasound image to be included in the region of interest. For example, the thresholds may be 90 percent probability, 80 percent probability, 70 percent probability, or any suitable probability. The boundary processor 150 is configured to determine the boundary (i.e., outer edge) of the region of interest and to superimpose a boundary on the ultrasound image delineating the region of interest in the ultrasound image. The location of the boundary overlaid on the ultrasound image is based on the threshold of the applied one of the plurality of segmentation sensitivity levels applied to the outputs of the probabilistic automatic segmentation model. For example, the boundary may be a thick delineation for a first segmentation sensitivity level, a thin delineation for a second segmentation sensitivity level, and an intermediate delineation for a third segmentation sensitivity level, among other things.

The boundary processor 150 may be configured to initially apply a first or default threshold corresponding with a first or default segmentation sensitivity level to the outputs of the probabilistic automatic segmentation model to determine the region of interest in the ultrasound image and to overlay the boundary on the ultrasound image. In response to a user-selection to change the segmentation sensitivity level to a different segmentation sensitivity level corresponding with a different threshold, the boundary processor 150 may be configured to re-apply the different threshold corresponding with the different user-selected segmentation sensitivity level to the outputs of the probabilistic automatic segmentation model to determine an adjusted region of interest in the ultrasound image and to dynamically overlay the adjusted boundary on the ultrasound image. In various embodiments, the initial default threshold corresponding with the initial default segmentation sensitivity level may be stored in association with a particular user (e.g., user profile), a particular ultrasound examination type, a particular ultrasound system 100, or the like. In an exemplary embodiment, the boundary processor 150 may be configured to update the initial default segmentation sensitivity level to be the last selected segmentation sensitivity level by a particular user, for a particular ultrasound examination type, at a particular ultrasound system 100, or the like.

The boundary processor 150 may be configured to cause a display system 134 to present the ultrasound image with the overlaid boundary and/or store the ultrasound image with the overlaid boundary at archive 138 and/or any suitable data storage medium. The boundary processor 150 may be configured to cause a display system 134 to present user interface tools for selecting and/or changing the segmentation sensitivity level. The user interface tools may comprise one or more of a scroll bar having different positions associated with different segmentation sensitivity levels, a list of user-selectable segmentation sensitivity levels, a tool illustrating increasable (+) and decreasable (−) segmentation sensitivity levels, an icon having selectable positions each associated with a different segmentation sensitivity level, and/or any suitable user interface tool for selectively changing the segmentation sensitivity level.

Figure 2:
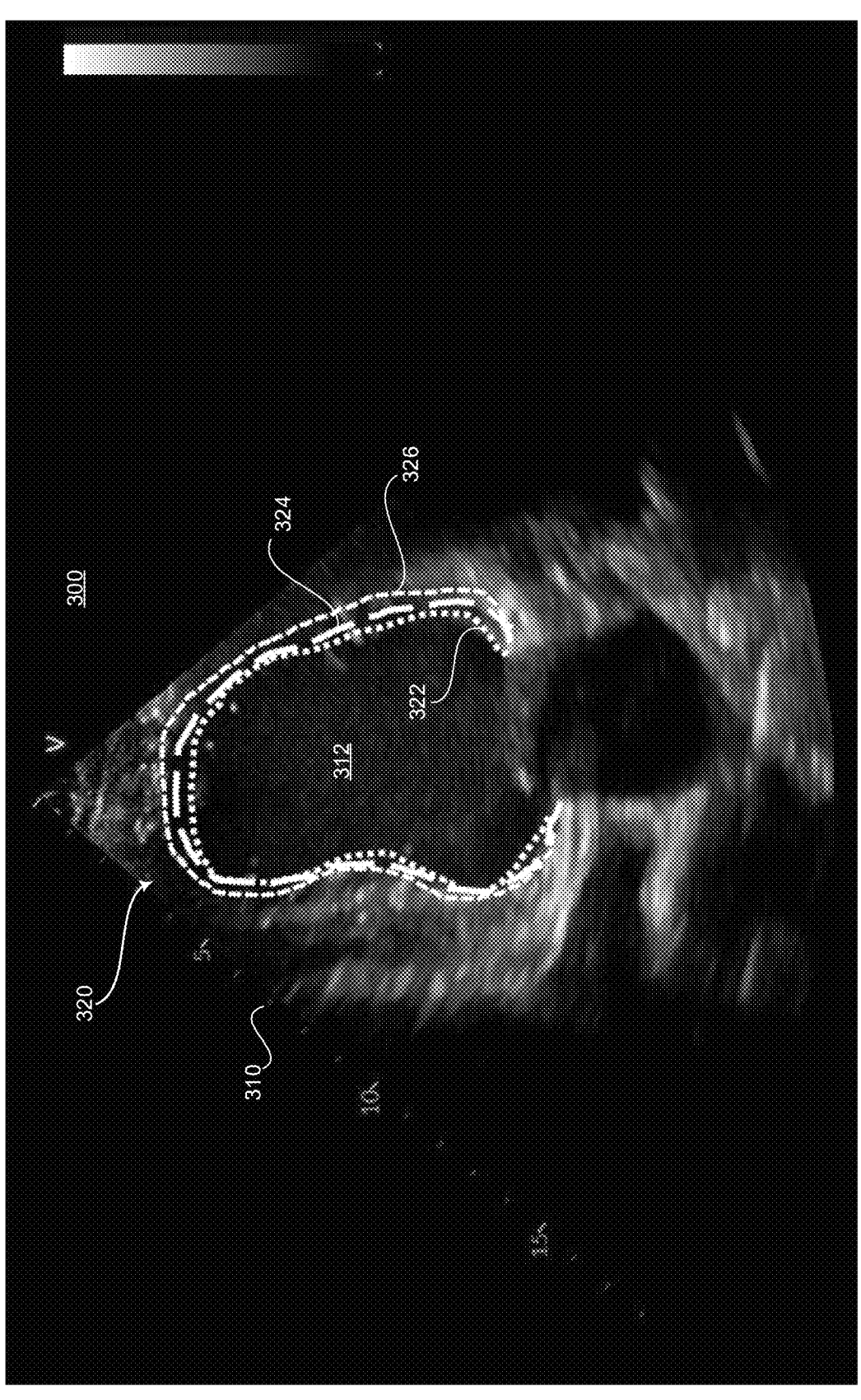
FIG. 2 is a display of an exemplary ultrasound image having a plurality of boundaries defining a segmented region of interest, each of the boundaries corresponding to a different threshold value associated with a different segmentation sensitivity level applied to outputs of a probabilistic automatic segmentation model, in accordance with various embodiments.

FIG. 2 is a display 300 of an exemplary ultrasound image 310 having a plurality of boundaries 320 defining a segmented region of interest 312, each of the boundaries 322, 324, 326 corresponding to a different threshold value associated with a different segmentation sensitivity level applied to outputs of a probabilistic automatic segmentation model, in accordance with various embodiments. Referring to FIG. 2, a display 300 of an ultrasound image 310 having boundaries 320 defining a region of interest 312 is shown. In the embodiment shown in FIG. 2, an apical two chamber (204) ultrasound image view 310 is shown where the region of interest 312 is a left ventricle. The boundaries 320 include a first boundary 322, a second boundary 324, and a third boundary 326. Each of the boundaries 322, 324, 326 corresponds to a different threshold value associated with a different segmentation sensitivity level applied, by the boundary processor 150 to outputs of a probabilistic automatic segmentation model of the segmentation processor 140. In practice, only one of the boundaries 322, 324, 326 is typically shown based on the default or selected segmentation sensitivity level. The first boundary 322 may correspond to a first segmentation sensitivity level (e.g., low) and may have a thin delineation of the region of interest 312. The second boundary 324 may correspond to a second segmentation sensitivity level (e.g., medium) and may have an intermediate delineation of the region of interest 312. The third boundary 326 may correspond to a third segmentation sensitivity level (e.g., high) and may have a thick delineation of the region of interest 312.

Figure 3:
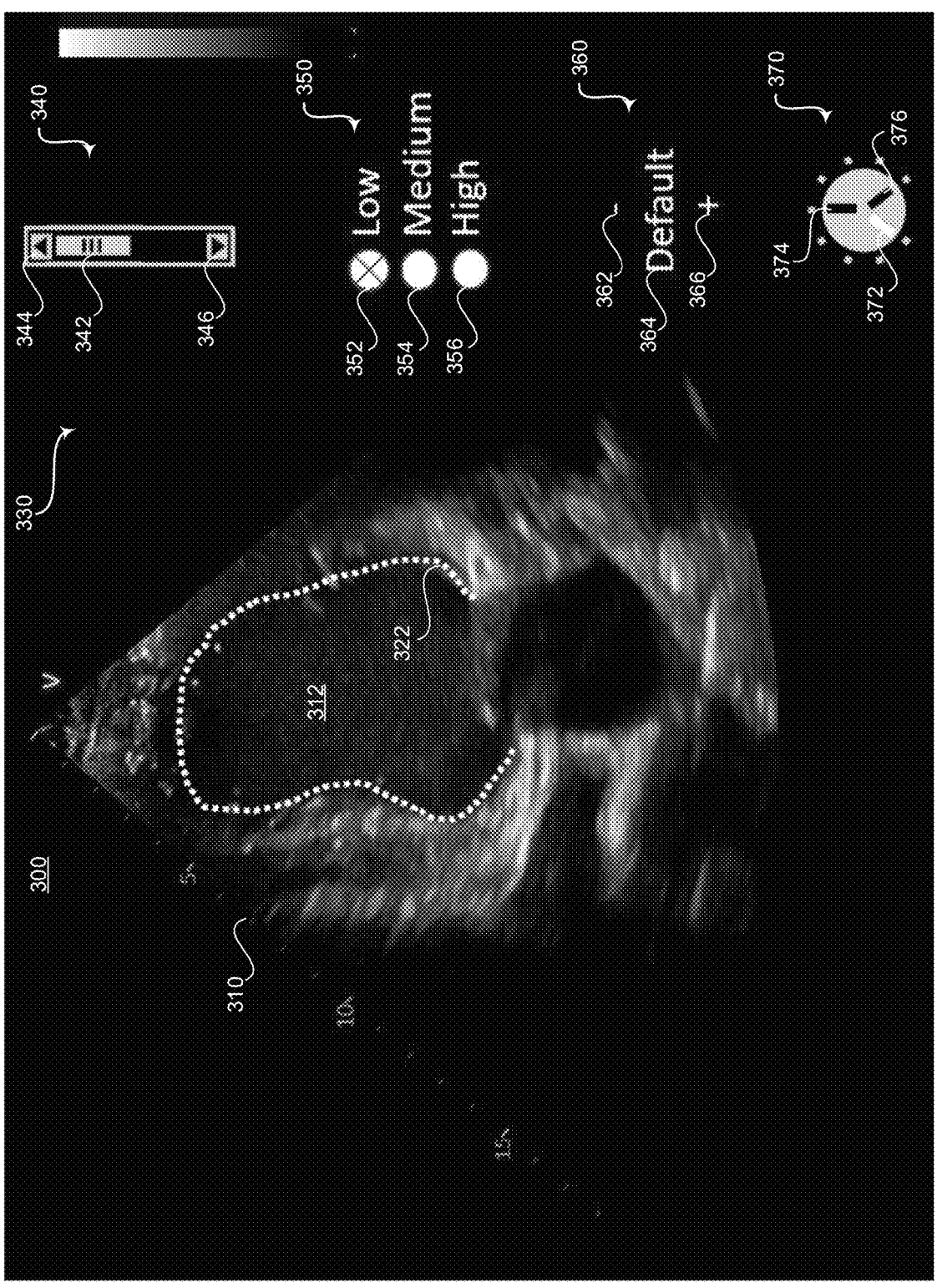
FIG. 3 is a display of exemplary user interface tools for selecting one of a plurality of segmentation sensitivity levels, each of the plurality of segmentation sensitivity levels associated with a different threshold value applied to outputs of a probabilistic automatic segmentation model to define a boundary of a region of interest, in accordance with various embodiments.

FIG. 3 is a display 300 of exemplary user interface tools 330 for selecting one of a plurality of segmentation sensitivity levels 342, 344, 346, 352, 354, 356, 362, 364, 366, 372, 374, 376, each of the plurality of segmentation sensitivity levels 342, 344, 346, 352, 354, 356, 362, 364, 366, 372, 374, 376 associated with a different threshold value applied to outputs of a probabilistic automatic segmentation model to define a boundary 322 of a region of interest 312, in accordance with various embodiments. Referring to FIG. 3, a display 300 of exemplary user interface tools 330 and an ultrasound image 310 having a boundary 322 defining a region of interest 312 is shown. In the embodiment shown in FIG. 3, an apical two chamber (2CH) ultrasound image view 310 is shown where the region of interest 312 is a left ventricle. The boundary 322 of the region of interest 312 overlaid on the ultrasound image 310 corresponds with the currently selected or default segmentation sensitivity level having an associated threshold that is applied to outputs of the probabilistic automatic segmentation model. The user interface tools 330 comprise a scroll bar 340, a list 350, an increasable (+) and decreasable (−) tool 360, and an icon having selectable positions 370. In practice, only one of the user interface tools 330 is typically shown for adjusting or selecting a segmentation sensitivity level. The scroll bar 340 may be presented vertically (as shown) or horizontally.

The scroll bar 340 may include an indicator 342 at a position corresponding with the currently selected segmentation sensitivity level. The indicator 342, which is shown at an upper position, may be dragged to a central position or a bottom position, for example. As another example, the indicator 342 may be moved by selecting the adjustment buttons 344, 346, turning a rotary encoder user inputs device 130, rotating a mouse wheel user input device 130, depressing arrows on a keyboard user input device 130, depressing dedicated buttons on a control panel user input device 130, and/or providing any suitable user input device 130 instruction. The position of the indicator 342 corresponds with a segmentation sensitivity level (e.g., low) having an associated threshold that is applied to outputs of the probabilistic automatic segmentation model to define the boundary 322 of the region of interest 312.

The list user interface tool 350 comprises a plurality of selectable segmentation sensitivity levels, such as low 352, medium 354, and high 356. The list 350 may include an indication of the currently selected segmentation sensitivity level (e.g., low) 352. The indication may be bold or highlighted text, underlining, a checkbox, shading, or any suitable indication. The indication may change or move depending on the selected segmentation sensitivity level, such as by touching or pointing to a segmentation sensitivity level 352, 354, 356 in the list 350, turning a rotary encoder user input device 130, rotating a mouse wheel user input device 130, depressing arrows of a keyboard user input device 130, depressing dedicated buttons on a control panel user input device 130, and/or any suitable user input device 130 instruction. The indication of the segmentation sensitivity level (e.g., low) identifies the segmentation sensitivity level having an associated threshold that is applied to outputs of the probabilistic automatic segmentation model to define the boundary 322 of the region of interest 312.

The increasable (+) and decreasable (−) tool 360 may include an indicator identifying the current segmentation sensitivity level (e.g., Default) by enlarged text, highlighting, underlining, shading, bold text, or any suitable indicator. The increasable (+) and decreasable (−) tool 360 may include selectable buttons for increasing 366, decreasing 362, or selecting a default 364 segmentation sensitivity level. As another example, increasable (+) and decreasable (−) tool 360 may increase or decrease the segmentation sensitivity levels via a rotary encoder user input device 130, mouse wheel user input device 130, arrows of a keyboard user input device 130, dedicated buttons on a control panel user input device 130, or any suitable user input device 130. The indication of the segmentation sensitivity level (e.g., enlarged "Default" text) identifies the segmentation sensitivity level having an associated threshold that is applied to outputs of the probabilistic automatic segmentation model to define the boundary 322 of the region of interest 312.

The icon 370 may include a plurality of selectable positions 372, 374, 376, each corresponding with a different selectable segmentation sensitivity level. The currently selected segmentation sensitivity level 372 may be identified by an indicator, such as colorizing, shading, and/or any suitable indicator. The indicator may be changed by selecting a different selectable position 374, 376, turning a rotary encoder user inputs device 130, rotating a mouse wheel user input device 130, depressing arrows on a keyboard user input device 130, and/or providing any suitable user input device 130 instruction. The position of the indicator 372 corresponds with a segmentation sensitivity level (e.g., low) having an associated threshold that is applied to outputs of the probabilistic automatic segmentation model to define the boundary 322 of the region of interest 312.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present the ultrasound images 310, the boundaries 320, the user interface tools 330, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound images 310, ultrasound images 310 overlaid with boundaries 320, outputs of a probabilistic automatic segmentation model executed by the segmentation processor 140, thresholds corresponding with segmentation sensitivity levels 342, 344, 346, 352, 354, 356, 362, 364, 366, 372, 374, 376, instructions for executing the probabilistic automatic segmentation model, instructions for applying the thresholds to the outputs of the probabilistic automatic segmentation model, instructing for generating and overlaying a boundary 322, 324, 326 on an ultrasound image 310, default segmentation sensitivity levels 342, 344, 346, 352, 354, 356, 362, 364, 366, 372, 374, 376, instructions for updating default segmentation sensitivity levels 342, 344, 346, 352, 354, 356, 362, 364, 366, 372, 374, 376, and/or any suitable images, information, and/or instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220, The training engine 210 may comprise suitable logic, circuitry, interfaces and/or code that may be operable to train the neurons of the deep neural network (e.g., artificial intelligence classification adapted segmentation network) inferenced (i.e., deployed) by the segmentation processor 140. For example, the probabilistic automatic segmentation model inferenced by the segmentation processor 140 may be trained to automatically determine probabilities of pixels being part of a region of interest 312. As an example, the training engine 210 may train the probabilistic automatic segmentation model deployed by the segmentation processor 140 to automatically determine probabilities of pixels being part of a region of interest 312 using database(s) 220 of classified anatomical structures, artificial structures, measurement endpoints, and/or any suitable region of interest 312. The classified regions of interest may include an input image and a ground truth binary image (i.e., mask) of the manually segmented region of interest. The training engine 210 may be configured to optimize the probabilistic automatic segmentation model by adjusting the weighting of the probabilistic automatic segmentation model to minimize a segmentation loss function between the input ground truth mask and an output predicted mask.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

FIG. 4 is a flow chart 400 illustrating exemplary steps 402-412 that may be utilized for defining a boundary 320, 322, 324, 326 of a region of interest 312 in an ultrasound image 310 by applying a threshold value corresponding to a user-selected segmentation sensitivity level 342, 344, 346, 352, 354, 356, 362, 364, 366, 372, 374, 376 to outputs of a probabilistic automatic segmentation model, in accordance with various embodiments. Referring to FIG. 4, there is shown a flow chart 400 comprising exemplary steps 402 through 412. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a signal processor 132 of an ultrasound system 100 or medical workstation receives an ultrasound image 310 having a plurality of pixels. For example, an ultrasound probe 104 of an ultrasound system WO may be navigated to perform an ultrasound scan. The acquired ultrasound image may be presented at a display system 134 of the ultrasound system 100, provided to a segmentation processor 140 of the signal processor 132 of the ultrasound system 100, and/or stored at archive 138 of the ultrasound system 100 and/or any suitable data storage medium. As another example, a signal processor 132 of a medical workstation may retrieve the ultrasound image 310 from archive 138 and/or any suitable data storage medium for presentation at a display system 134 of the medical workstation.

At step 404, the signal processor 132 processes the ultrasound image 310 to output a probability of each of the plurality of pixels being in a region of interest 312. For example, a segmentation processor 132 of the signal processor may comprise a probabilistic automatic segmentation model that receives the ultrasound image 310 having the plurality of pixels and outputs the probability of each pixel being part of the region of interest 312. The region of interest 312 may be an anatomical structure, an artificial structure, measurement endpoints, or the like. The probabilistic automatic segmentation model may comprise image analysis algorithms, artificial intelligence algorithms, computer vision algorithms, one or more deep neural networks (e.g., a convolutional neural network) and/or may utilize any suitable form of image analysis techniques or machine learning processing functionality configured to automatically process and output probabilities that pixels of an ultrasound image 310 are part of a region of interest 312. The probabilistic automatic segmentation model executed by the segmentation processor 140 may provide the outputted probabilities to a boundary processor 150 of the signal processor 132 and/or store the probabilities at archive 138 and/or any suitable data storage medium.

At step 406, the signal processor 132 applies a first threshold value to determine a boundary 320, 322, 324, 326 of the region of interest 312 in the ultrasound image 310. The first threshold value corresponds with a first segmentation sensitivity level of a plurality of segmentation sensitivity levels 342, 344, 346, 352, 354, 356, 362, 364, 366, 372, 374, 376. For example, a boundary processor 150 of the signal processor 132 may be configured to apply a first (e.g., default) threshold corresponding to one of a plurality of segmentation sensitivity levels 342, 344, 346, 352, 354, 356, 362, 364, 366, 372, 374, 376 to determine a boundary 320, 322, 324, 326 of the region of interest 312. Each of the plurality of segmentation sensitivity levels 342, 344, 346, 352, 354, 356, 362, 364, 366, 372, 374, 376 corresponds with a different threshold. For example, the plurality of segmentation sensitivity levels 342, 344, 346, 352, 354, 356, 362, 364, 366, 372, 374, 376 may comprise two (2), three (3), five (5), ten (10), or any suitable number of segmentation sensitivity levels. The thresholds associated with each of the segmentation sensitivity levels 342, 344, 346, 352, 354, 356, 362, 364, 366, 372, 374, 376 are applied by the boundary processor 150 to determine the pixels of the ultrasound image 310 to be included in the region of interest 312. For example, the thresholds may be 90 percent probability, 80 percent probability, 70 percent probability, or any suitable probability. The boundary processor 150 is configured to determine the boundary (i.e., outer edge) 320, 322, 324, 326 of the region of interest 312.

At step 408, the signal processor 132 causes a display system 134 of the ultrasound system 100 or workstation to present the ultrasound image with the boundary 320, 322, 324, 326 overlaid on the ultrasound image 310. For example, the boundary processor 150 of the signal processor 132 may be configured to superimpose a boundary 320, 322, 324, 326 on the ultrasound image 310 delineating the region of interest 312 in the ultrasound image 310. The location of the boundary 320, 322, 324, 326 overlaid on the ultrasound image 310 is based on the threshold of the applied one of the plurality of segmentation sensitivity levels applied to the outputs of the probabilistic automatic segmentation model. For example, the boundary 320, 322, 324, 326 may be a thick delineation for a first segmentation sensitivity level, a thin delineation for a second segmentation sensitivity level, and an intermediate delineation for a third segmentation sensitivity level, among other things. The boundary processor 150 may be configured to cause a display system 134 to present, with the ultrasound image 310 and superimposed boundary 320, 322, 324, 326, user interface tools 330 for selecting and/or changing the segmentation sensitivity level. The user interface tools 330 may comprise one or more of a scroll bar 340 having different positions associated with different segmentation sensitivity levels, a list 350 of user-selectable segmentation sensitivity levels, a tool 360 illustrating increasable (+) and decreasable (−) segmentation sensitivity levels, an icon 370 having selectable positions 372, 374, 376 each associated with a different segmentation sensitivity level, and/or any suitable user interface tool 330 for selectively changing the segmentation sensitivity level.

At step 410, the signal processor 132 receives a user selection of a second segmentation level from the plurality of segmentation sensitivity levels 342, 344, 346, 352, 354, 356, 362, 364, 366, 372, 374, 376. The second segmentation sensitivity level corresponds with a second threshold value different from the first threshold value. For example, the boundary processor 150 of the signal processor 132 may be configured to receive a selection of a different segmentation sensitivity level via the user interface tools 330 and/or a user input device 130.

At step 412, the signal processor 132 may cause a display system 134 of the ultrasound system 100 or workstation to dynamically update the boundary 320, 322, 324, 326 overlaid on the ultrasound image 310 based on the second threshold value. For example, in response to a user-selection to change the segmentation sensitivity level to a different segmentation sensitivity level corresponding with a different threshold at step 410, the boundary processor 150 may be configured to re-apply the different threshold corresponding with the different user-selected segmentation sensitivity level to the outputs of the probabilistic automatic segmentation model to determine an adjusted region of interest 312 in the ultrasound image 310 and to dynamically overlay the adjusted boundary 320, 322, 324, 326 on the ultrasound image 310. In various embodiments, the initial default threshold corresponding with the initial default segmentation sensitivity level applied at step 406 may be stored in association with a particular user (e.g., user profile), a particular ultrasound examination type, a particular ultrasound system 100, or the like. In an exemplary embodiment, the boundary processor 150 may be configured to update the initial default segmentation sensitivity level to be the last selected segmentation sensitivity level by a particular user, for a particular ultrasound examination type, at a particular ultrasound system 100, or the like.

Aspects of the present disclosure provide a method 400 and system 100 for defining a boundary 320, 322, 324, 326 of a region of interest 312 in an ultrasound image 310 by applying a threshold value corresponding to a user-selected segmentation sensitivity level 342, 344, 346, 352, 354, 356, 362, 364, 366, 372, 374, 376 to outputs of a probabilistic automatic segmentation model. In accordance with various embodiments, the method 400 may comprise receiving 402, by at least one processor 132, an ultrasound image 310 having a plurality of pixels. The method 400 may comprise automatically processing 404, by the at least one processor 132, 140 executing a segmentation model, the ultrasound image 300 to output a probability of each of the plurality of pixels being in a region of interest 312. The method 400 may comprise applying 406, by the at least one processor 132,

150, a first threshold value to determine a boundary 320, 322, 324, 326 of the region of interest 312. The first threshold value corresponds with a first segmentation sensitivity level of a plurality of segmentation sensitivity levels 342, 344, 346, 352, 354, 356, 362, 364, 366, 372, 374, 376. The method 400 may comprise causing, by the at least one processor 132, 150, a display system 134 to present 408 the ultrasound image 310 with the boundary 320, 322, 324, 326 overlaid on the ultrasound image 310. The method 400 may comprise receiving 410, by the at least one processor 132, 150, a user selection of a second segmentation sensitivity level from the plurality of segmentation sensitivity levels 342, 344, 346, 352, 354, 356, 362, 364, 366, 372, 374, 376. The second segmentation sensitivity level corresponds with a second threshold value different from the first threshold value. The method 400 may comprise dynamically updating 412, by the at least one processor 132, 150, the boundary 320, 322, 324, 326 overlaid on the ultrasound image 310 at the display system 134 based on the second threshold value.

In a representative embodiment, each of the plurality of segmentation sensitivity levels 342, 344, 346, 352, 354, 356, 362, 364, 366, 372, 374, 376 is a preset having a different pre-defined threshold value. In an exemplary embodiment, the method 400 may comprise presenting 408 a user interface tool 350 having a list of the plurality of segmentation sensitivity levels 352, 354, 356 at the display system 134 with the ultrasound image 310. Each of the plurality of segmentation sensitivity levels 352, 354, 356 presented in the list being user-selectable. In various embodiments, the method 400 may comprise presenting 408 a user interface tool 340, 370 having a plurality of selectable positions 342, 344, 346, 372, 374, 376 at the display system 134 with the ultrasound image 310. Each of the plurality of selectable positions 342, 344, 346, 372, 374, 376 corresponding with one of the plurality of segmentation sensitivity levels 342, 344, 346, 352, 354, 356, 362, 364, 366, 372, 374, 376. In certain embodiments, the first threshold value corresponding with the first segmentation sensitivity level is a default. The method 400 may further comprise updating 412 the default to the second threshold value corresponding with the second segmentation sensitivity level based on the user selection 410. In a representative embodiment, the method 400 may comprise storing 412 the default in association with one or both of a specific user profile or a specific ultrasound system 100. In an exemplary embodiment, the region of interest 312 is one of an anatomical structure 312, an artificial structure, or measurement endpoints. In certain embodiments, the segmentation model is an artificial intelligence segmentation model.

Various embodiments provide a system 100 for defining a boundary 320, 322, 324, 326 of a region of interest 312 in an ultrasound image 310 by applying a threshold value corresponding to a user-selected segmentation sensitivity level 342, 344, 346, 352, 354, 356, 362, 364, 366, 372, 374, 376 to outputs of a probabilistic automatic segmentation model. The system 100 may comprise at least one processor 132, 140, 150, and a display system 134. The at least one processor 132 may be configured to receive an ultrasound image 310 having a plurality of pixels. The at least one processor 132, 140 may be configured to automatically process the ultrasound image 310 by executing a segmentation model to output a probability of each of the plurality of pixels being in a region of interest 312. The at least one processor 132, 150 may be configured to apply a first threshold value to determine a boundary 320, 322, 324, 326 of the region of interest 312. The first threshold value corresponds with a first segmentation sensitivity level of a plurality of segmentation sensitivity levels 342, 344, 346, 352, 354, 356, 362, 364, 366, 372, 374, 376. The at least one processor 132, 150 may be configured to cause a display system 134 to present the ultrasound image 310 with the boundary 320, 322, 324, 326 overlaid on the ultrasound image 310. The at least one processor 132, 150 may be configured to receive a user selection of a second segmentation sensitivity level from the plurality of segmentation sensitivity levels 342, 344, 346, 352, 354, 356, 362, 364, 366, 372, 374, 376. The second segmentation sensitivity level corresponds with a second threshold value different from the first threshold value. The at least one processor 132, 150 may be configured to dynamically update the boundary 320, 322, 324, 326 overlaid on the ultrasound image 310 at the display system 134 based on the second threshold value. The display system 134 may be configured to present the ultrasound image 310 with the boundary 320, 322, 324, 326 overlaid on the ultrasound image 310.

In an exemplary embodiment, each of the plurality of segmentation sensitivity levels 342, 344, 346, 352, 354, 356, 362, 364, 366, 372, 374, 376 is a preset having a different pre-defined threshold value. In certain embodiments, the at least one processor 132, 150 is configured to cause the display system 134 to present a user interface tool 350 having a list of the plurality of segmentation sensitivity levels 352, 354, 356 with the ultrasound image 310. Each of the plurality of segmentation sensitivity levels 352, 354, 356 presented in the list being user-selectable.

In various embodiments, the at least one processor 132, 150 is configured to cause the display system 134 to present a user interface tool 340, 370 having a plurality of selectable positions 342, 344, 346, 372, 374, 376 with the ultrasound image 310. Each of the plurality of selectable positions 342, 344, 346, 372, 374, 376 corresponding with one of the plurality of segmentation sensitivity levels 342, 344, 346, 352, 354, 356, 362, 364, 366, 372, 374, 376. In a representative embodiment, the first threshold value corresponding with the first segmentation sensitivity level is a default. The at least one processor 132, 150 may be configured to update the default to the second threshold value corresponding with the second segmentation sensitivity level based on the user selection. The at least one processor 132, 150 may be configured to store the default in association with one or both of a specific user profile or a specific ultrasound system 100. In an exemplary embodiment, the region of interest 312 is one of an anatomical structure 312, an artificial structure, or measurement endpoints. In various embodiments, the segmentation model is an artificial intelligence segmentation model.

Certain embodiments provide a non-transitory computer readable medium having stored thereon, a computer program having at least one code section. The at least one code section is executable by a machine for causing a system to perform steps 400. The steps 400 may comprise receiving 402 an ultrasound image 310 having a plurality of pixels. The steps 400 may comprise automatically processing 404 the ultrasound image 310 by executing a segmentation model to output a probability of each of the plurality of pixels being in a region of interest 312. The steps 400 may comprise applying 406 a first threshold value to determine a boundary 320, 322, 324, 326 of the region of interest 312. The first threshold value corresponds with a first segmentation sensitivity level of a plurality of segmentation sensitivity levels 342, 344, 346, 352, 354, 356, 362, 364, 366, 372, 374, 376. The steps 400 may comprise causing a display system 134 to present 408 the ultrasound image 310 with the boundary 320, 322, 324, 326 overlaid on the ultrasound image 310. The steps 400 may receiving 410 a user selection of a second segmentation sensitivity level from the plurality of segmentation sensitivity levels 342, 344, 346, 352, 354, 356, 362, 364, 366, 372, 374, 376. The second segmentation sensitivity level corresponds with a second threshold value different from the first threshold value. The steps 400 may dynamically updating 412 the boundary 320, 322, 324, 326 overlaid on the ultrasound image 310 at the display system 134 based on the second threshold value.

In various embodiments, each of the plurality of segmentation sensitivity levels 342, 344, 346, 352, 354, 356, 362, 364, 366, 372, 374, 376 is a preset having a different pre-defined threshold value. In certain embodiments, the steps 400 may comprise presenting 408 a user interface tool 350 having a list of the plurality of segmentation sensitivity levels 352, 354, 356 at the display system 134 with the ultrasound image 310. Each of the plurality of segmentation sensitivity levels 352, 354, 356 presented in the list being user-selectable. In a representative embodiment, the steps 400 may comprise presenting 408 a user interface tool 340, 370 having a plurality of selectable positions 342, 344, 346, 372, 374, 376 at the display system 134 with the ultrasound image 310. Each of the plurality of selectable positions 342, 344, 346, 372, 374, 376 corresponding with one of the plurality of segmentation sensitivity levels 342, 344, 346, 352, 354, 356, 362, 364, 366, 372, 374, 376. In an exemplary embodiment, the first threshold value corresponding with the first segmentation sensitivity level is a default. The steps 400 may comprise updating 412 the default to the second threshold value corresponding with the second segmentation sensitivity level based on the user selection 410. The steps 400 may comprise storing 412 the default in association with one or both of a specific user profile or a specific ultrasound system 100.

As utilized herein the term "circuitry" refers to physical electronic components (i.e. hardware) and any software and/or firmware ("code") Which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for defining a boundary of a region of interest in an ultrasound image by applying a threshold value corresponding to a user-selected segmentation sensitivity level to outputs of a probabilistic automatic segmentation model.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:

receiving, by at least one processor, an ultrasound image having a plurality of pixels;

automatically processing, by the at least one processor executing a segmentation model, the ultrasound image to output a probability of each of the plurality of pixels being in a region of interest;

applying, by the at least one processor, a first threshold value to the probability of each of the plurality of pixels output based on the automatic processing of the ultrasound image, wherein the applying the first threshold value determines a boundary of the region of interest, wherein the first threshold value corresponds with a first segmentation sensitivity level of a plurality of segmentation sensitivity levels;

causing, by the at least one processor, a display system to present the ultrasound image with the boundary overlaid on the ultrasound image;

receiving, by the at least one processor, a user selection of a second segmentation sensitivity level from the plurality of segmentation sensitivity levels, wherein the second segmentation sensitivity level corresponds with a second threshold value different from the first threshold value; and dynamically updating, by the at least one processor, the boundary overlaid on the ultrasound image at the display system by applying the second threshold value to the probability of each of the plurality of pixels output based on the automatic processing of the ultrasound image.

2. The method of claim 1, wherein each of the plurality of segmentation sensitivity levels is a preset having a different pre-defined threshold value.

3. The method of claim 1, comprising presenting a user interface tool having a list of the plurality of segmentation sensitivity levels at the display system with the ultrasound image, each of the plurality of segmentation sensitivity levels presented in the list being user-selectable.

4. The method of claim 1, comprising presenting a user interface tool having a plurality of selectable positions at the display system with the ultrasound image, each of the plurality of selectable positions corresponding with one of the plurality of segmentation sensitivity levels.

5. The method of claim 1, wherein the first threshold value corresponding with the first segmentation sensitivity level is a default, and further comprising updating the default to the second threshold value corresponding with the second segmentation sensitivity level based on the user selection.

6. The method of claim 5, comprising storing the default in association with one or both of a specific user profile or a specific ultrasound system.

7. The method of claim 1, wherein the region of interest is one of an anatomical structure, an artificial structure, or measurement endpoints.

8. The method of claim 1, wherein the segmentation model is an artificial intelligence segmentation model.

9. A system comprising:

at least one processor configured to:

receive an ultrasound image having a plurality of pixels;

automatically process the ultrasound image by executing a segmentation model to output a probability of each of the plurality of pixels being in a region of interest;

apply a first threshold value to the probability of each of the plurality of pixels output based on the automatic processing of the ultrasound image, wherein application of the first threshold value determines a boundary of the region of interest, wherein the first threshold value corresponds with a first segmentation sensitivity level of a plurality of segmentation sensitivity levels;

cause a display system to present the ultrasound image with the boundary overlaid on the ultrasound image;

receive a user selection of a second segmentation sensitivity level from the plurality of segmentation sensitivity levels, wherein the second segmentation sensitivity level corresponds with a second threshold value different from the first threshold value; and dynamically update the boundary overlaid on the ultrasound image at the display system by applying the second threshold value to the probability of each of the plurality of pixels output based on the automatic processing of the ultrasound image; and the display system configured to present the ultrasound image with the boundary overlaid on the ultrasound image.

10. The system of claim 9, wherein each of the plurality of segmentation sensitivity levels is a preset having a different pre-defined threshold value.

11. The system of claim 9, wherein the at least one processor is configured to cause the display system to present a user interface tool having a list of the plurality of segmentation sensitivity levels with the ultrasound image, each of the plurality of segmentation sensitivity levels presented in the list being user-selectable.

12. The system of claim 9, wherein the at least one processor is configured to cause the display system to present a user interface tool having a plurality of selectable positions with the ultrasound image, each of the plurality of selectable positions corresponding with one of the plurality of segmentation sensitivity levels.

13. The system of claim 9, wherein:

the first threshold value corresponding with the first segmentation sensitivity level is a default; and the at least one processor is configured to:

update the default to the second threshold value corresponding with the second segmentation sensitivity level based on the user selection, and store the default in association with one or both of a specific user profile or a specific ultrasound system.

14. The system of claim 9, wherein the region of interest is one of an anatomical structure, an artificial structure, or measurement endpoints.

15. The system of claim 9, wherein the segmentation model is an artificial intelligence segmentation model.

16. A non-transitory computer readable medium having stored thereon, a computer program having at least one code section, the at least one code section being executable by a machine for causing an ultrasound system to perform steps comprising:

receiving an ultrasound image having a plurality of pixels;

automatically processing the ultrasound image by executing a segmentation model to output a probability of each of the plurality of pixels being in a region of interest;

applying a first threshold value to the probability of each of the plurality of pixels output based on the automatic processing of the ultrasound image, wherein:

the applying the first threshold value determines a boundary of the region of interest, the first threshold value corresponds with a first segmentation sensitivity level of a plurality of segmentation sensitivity levels, and the first threshold value corresponding with the first segmentation sensitivity level is a default;

causing a display system to present the ultrasound image with the boundary overlaid on the ultrasound image;

receiving a user selection of a second segmentation sensitivity level from the plurality of segmentation sensitivity levels, wherein the second segmentation sensitivity level corresponds with a second threshold value different from the first threshold value;

dynamically updating the boundary overlaid on the ultrasound image at the display system by applying the second threshold value to the probability of each of the plurality of pixels output based on the automatic processing of the ultrasound image;

updating the default to the second threshold value corresponding with the second segmentation sensitivity level based on the user selection; and storing the default in association with one or both of a specific user profile or a specific ultrasound system.

17. The non-transitory computer readable medium of claim 16, wherein each of the plurality of segmentation sensitivity levels is a preset having a different pre-defined threshold value.

18. The non-transitory computer readable medium of claim 16, comprising presenting a user interface tool having a list of the plurality of segmentation sensitivity levels at the display system with the ultrasound image, each of the plurality of segmentation sensitivity levels presented in the list being user-selectable.

19. The non-transitory computer readable medium of claim 16, comprising presenting a user interface tool having a plurality of selectable positions at the display system with the ultrasound image, each of the plurality of selectable positions corresponding with one of the plurality of segmentation sensitivity levels.

* * * * *